United States Patent
Murthy et al.

(10) Patent No.: US 10,482,313 B2
(45) Date of Patent: Nov. 19, 2019

(54) METHOD AND SYSTEM FOR CLASSIFICATION OF ENDOSCOPIC IMAGES USING DEEP DECISION NETWORKS

(71) Applicants: SIEMENS HEALTHCARE GMBH, Erlangen (DE); SIEMENS CORPORATION, Princeton, NJ (US)

(72) Inventors: Venkatesh N. Murthy, Amherst, MA (US); Vivek Kumar Singh, Princeton, NJ (US); Shanhui Sun, Princeton, NJ (US); Subhabrata Bhattacharya, Seattle, WA (US); Kai Ma, Princeton, NJ (US); Ali Kamen, Skillman, NJ (US); Bogdan Georgescu, Plainsboro, NJ (US); Terrence Chen, Princeton, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 69 days.

(21) Appl. No.: 15/756,263

(22) PCT Filed: Sep. 29, 2016

(86) PCT No.: PCT/EP2016/073209
§ 371 (c)(1),
(2) Date: Feb. 28, 2018

(87) PCT Pub. No.: WO2017/055412
PCT Pub. Date: Apr. 6, 2017

(65) Prior Publication Data
US 2018/0247107 A1 Aug. 30, 2018

Related U.S. Application Data

(60) Provisional application No. 62/235,103, filed on Sep. 30, 2015.

(51) Int. Cl.
*G06K 9/00* (2006.01)
*G06K 9/46* (2006.01)
(Continued)

(52) U.S. Cl.
CPC ....... *G06K 9/00147* (2013.01); *G06K 9/4628* (2013.01); *G06T 7/0012* (2013.01);
(Continued)

(58) Field of Classification Search
CPC .......... G06K 2209/05; G06K 9/00147; G06K 9/4628; G06T 2207/10068;
(Continued)

(56) References Cited

U.S. PATENT DOCUMENTS

2018/0075599 A1* 3/2018 Tajbakhsh ............ A61B 5/0084

OTHER PUBLICATIONS

Markou, Markos, and Sameer Singh. "A neural network-based novelty detector for image sequence analysis." IEEE Transactions on Pattern Analysis and Machine Intelligence28.10 (2006): 1664-1677. (Year: 2006).*
(Continued)

*Primary Examiner* — Nirav G Patel

(57) ABSTRACT

A method and system for classification of endoscopic images is disclosed. An initial trained deep network classifier is used to classify endoscopic images and determine confidence scores for the endoscopic images. The confidence score for each endoscopic image classified by the initial trained deep network classifier is compared to a learned confidence threshold. For endoscopic images with confidence scores higher than the learned threshold value, the classification result from the initial trained deep network classifier is output. Endoscopic images with confidence scores lower than the learned confidence threshold are classified using a first specialized network classifier built on a feature space of the initial trained deep network classifier.

32 Claims, 8 Drawing Sheets

(51) Int. Cl.
*G06T 7/00* (2017.01)
*G16H 30/20* (2018.01)

(52) U.S. Cl.
CPC .................. *G06K 2209/05* (2013.01); *G06T 2207/10068* (2013.01); *G06T 2207/20084* (2013.01); *G06T 2207/30096* (2013.01); *G16H 30/20* (2018.01)

(58) Field of Classification Search
CPC . G06T 2207/20084; G06T 2207/30096; G06T 7/0012; G16H 30/20
See application file for complete search history.

(56) References Cited

OTHER PUBLICATIONS

Breuskin, David, et al. "Confocal laser endomicroscopy in neurosurgery: a new technique with much potential." Minimally invasive surgery 2013 (2013). (Year: 2013).*
International Search Report for Corresponding International Patent Application No. PCT/EP2016/073209, dated Dec. 16, 2016.
Lecun Yann et al., "Gradient-Based Learning Applied to Document Recognition", Proceedings of the IEEE, New York, US, vol. 86, No. 11, Nov. 1, 1998, pp. 2278-2323.
Drucker Harris et al, "Improving Performance in Neural Networks Using a Boosting Algorithm", Jan. 1, 1993, XP55326455, Retrieved from the Internet: URL: https://papers.nips.cc/papers/593-improving-performance-in-neural-networks-using-a-boosting-algorithm.pdf, p. 42-49.

* cited by examiner

METHOD AND SYSTEM FOR CLASSIFICATION OF ENDOSCOPIC IMAGES USING DEEP DECISION NETWORKS

This application is a National Phase of PCT/EP2016/073209, filed Sep. 29, 2016, which claims the benefit of U.S. Provisional Application No. 62/235,103, filed Sep. 30, 2015, the disclosure of which is herein incorporated by reference.

BACKGROUND OF THE INVENTION

The present invention relates to classification of endoscopic images, and more particularly, to classification of endoscopic images using deep learning based networks to detect endoscopic images having abnormal cell or tissue growth.

Endoscopic image analysis plays an important role in visual diagnosis of lethal medical conditions originating primarily in the gastrointestinal tract, respiratory tract, or other vital tracts of the human body. Early and precise detection of many of these conditions can increase the chances of survival of an ailing patient through appropriate clinical procedures. For example, the relative five year survival rate of colorectal cancer is about 90% when diagnosed at an early polyp stage before it has spread. Similarly, meningioma, a benign intra-cranial tumor condition occurring in approximately seven of every 100,000 people, can be treated surgically or radiologically if detected early, thereby drastically reducing the chances of its malignancy.

Currently, clinicians visually scan endoscopic images, typically captured through endoscopic probes, for abnormal cell or tissue growth in the region under observation. Such manual screening procedures can be tedious, as a single endoscopic probe typically generates a very large number of images. Furthermore, since the screening relies heavily on the dexterity of the clinician in charge, cases of missed detection are not uncommon. Accordingly, automated computer aided diagnosis (CAD) solutions are desirable that can efficiently screen out irrelevant endoscopic images and detect endoscopic images in which abnormal cell or tissue growth is present.

BRIEF SUMMARY OF THE INVENTION

The present disclosure provides a method and system for classifying endoscopic images using a deep decision network. Embodiments of the present invention present a deep decision network (DDN) that classifies endoscopic images to detect endoscopic images is which abnormal cell or tissue growth is present. Embodiments of the present invention train DDN in a learning phase by automatically building a network that greedily discards samples that are classified with high confidence scores by an initial trained deep network classifier and concentrates only on challenging samples to train one or more subsequent specialized deep network classifiers. Embodiments of the present invention use a trained DDN to classify endoscopic images, such that only the initial trained deep network classifier is used for endoscopic images that are classified with high confidence scores and the one or more subsequent specialized deep network classifiers are used to classify challenging endoscopic images.

In one embodiment, an endoscopic image is classified and a confidence score is determined for the endoscopic image using an initial trained deep network classifier. The confidence score for the endoscopic image is compared to a learned confidence threshold. In response to a determination that the confidence score for the endoscopic image is higher than the learned confidence threshold, the classification of the endoscopic image by the initial trained deep network classifier is output. In response to a determination that the confidence score for the endoscopic image is not higher than the learned confidence threshold, the endoscopic image is classified with a first specialized network classifier built on a feature space of the initial trained deep network classifier.

In another embodiment, a plurality of endoscopic images are received. Each of the plurality of endoscopic images is classified and a confidence score is determined for each of the plurality of endoscopic images using an initial trained deep network classifier. The confidence score for each of the plurality of endoscopic images is compared to a learned confidence threshold to determine a highly confident subset of the plurality of endoscopic images and a confusion subset of the plurality of endoscopic images. Classification results from the initial trained deep network classifier are output for the highly confident subset of the plurality of endoscopic images. Each of the confusion subset of the plurality of endoscopic images is classified using one or more specialized network classifiers.

These and other advantages of the embodiments will be apparent to those of ordinary skill in the art by reference to the following detailed description and the accompanying drawings.

DETAILED DESCRIPTION

The present invention relates to classification of endoscopic images using deep decision networks. Embodiments of the present invention are described herein to give a visual understanding of the method for automated classification of endoscopic images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

In practice, different endoscopic imaging procedures are used to observe different regions of the body and to scan for different medical conditions. For example, in capsule endoscopy, an encapsulated wireless video camera is used to capture images from the gastro-intestinal tract. Confocal laser endomiscroscopy (CLE) probes are used by neurosurgeons to provide surgical guidance to examiner brain tissues for intracranial tumors. Although these application scenarios are different, their fundamental objective involves searching for visually discriminative patterns that can be decisive for a binary classification task of segregating positive samples in which abnormal tissue, such as tumors or polyps, are present from negative samples in which no abnormal tissue is not present. Embodiments of the present invention can be applied to classify any type of endoscopic image data.

Figure 1:
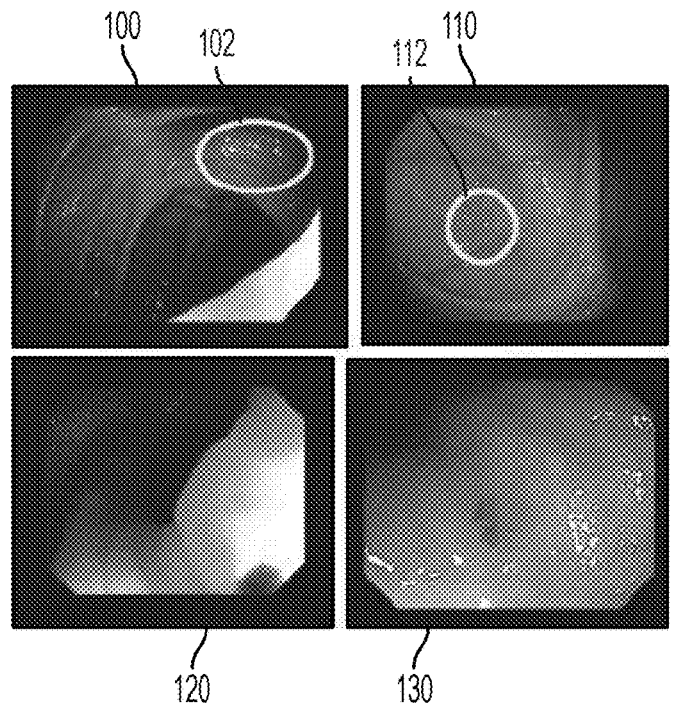
FIG. 1 illustrates exemplary endoscopic images obtained from a colonoscopic examination.
Figure 2:
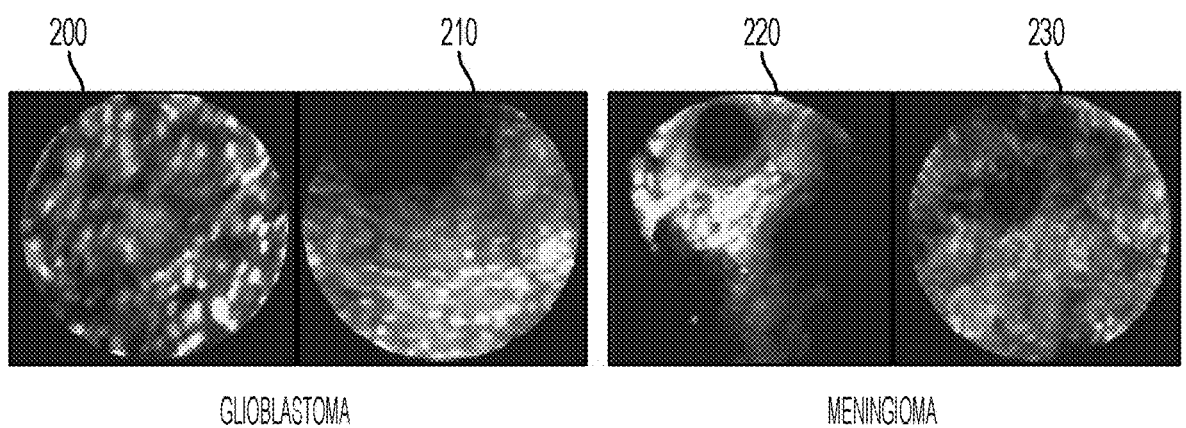
FIG. 2 illustrates exemplary CLE images showing glioblastoma and meningioma.

In one embodiment of the present invention, a deep decision network (DDN) is used to classify colonoscopic images to filter out a large number of negative images that do not contain colon polyps and to detect positive images that do contain colon polyps. FIG. 1 illustrates exemplary endoscopic images obtained from a colonoscopic examination. As shown in FIG. 1, images 100 and 110 contain colon polyps 102 and 112, respectively, which appear as visually translucent blobs in the GI tract. Images 120 and 130 do not contain colon polyps. In another embodiment of the present invention, a DDN is used to classify CLE images of brain tissue in order to identify malignant cases of brain tumors (glioblastoma) from benign brain tumors (meningioma) in CLE images containing either of the two. FIG. 2 illustrates exemplary CLE images showing glioblastoma and meningioma. As shown in FIG. 2, images 200 and 210 are CLE images of glioblastoma tissue, which are often characterized by sharp granular patterns. Images 220 and 230 are CLE images of meningioma tissue, which are often characterized by smooth homogenous patterns. Both of these classification scenarios have their own challenges. The classification of colonoscopic images has several non-trivial inhibitors encountered by conventional computer vision systems including non-uniform illumination from light emitting diodes, noise from bubbles and bowel fluids, occlusion posed by anatomical complexity, and large degrees of variation in shape and size of polyps. The classification of CLE images of brain tissue is limited with the low resolution of current CLE imagery, motion artifacts, and often presence of both types of tissue in the probing area. Embodiments of the present invention provide a method and system that improve classification results in both scenarios.

Conventional techniques computer vision techniques for Automatic visual analysis of images pertaining to the aforementioned domains are typically based on variants of Bag of visual Words (BoW) based computational frameworks owing to their simplicity. These methods typically involve extraction of features from an image, followed by a vector quantization step based on a pre-defined visual vocabulary, which results in an intermediate compact representation of an image that can be ingested as a training sample for supervised classifiers. While these methods are somewhat effective, they consistently fail to leverage on the data-driven aspect of the problem as all three steps, feature extraction, generation of the intermediate representation, and finally the classification are mutually independent.

Recently, deep learning based approaches have been used, in which deep neural networks are applied to generic classification tasks. However, training deep neural networks from image data is a challenging task that often requires thorough experimentation on large datasets. Due to a lack of a large amount of training data, the trained deep network architecture often overtly optimizes itself for only the training data, and performs poorly with unseen test samples. In Y. Bar, et al., "Chest Pathology Detection Using Deep Learning with Non-Medical Training," in 12$^{th}$ IEEE International Symposium on Biomedical Engineering, 2015, pp. 294-297, this issue is avoided by employing a pre-trained convolutional neural network whose parameters are learned from a large scale non-medical image database. This technique has demonstrated high performance on a medical application of chest pathology detection in X-ray images. However, this technique is not conclusive for any cross-domain application. Embodiments of the present invention provide a computational framework to generate a deep network architecture during the parameter learning phase with limited training data, yet without over-fitting the training.

Given a classification task, training a performant deep network is a challenging task since there are no well established guidelines for designing the network architecture. Accordingly, training a deep network may involve thorough experimentation and statistical analysis. Although going deeper in the neural network design may be effective in some cases, it also increases the risk of over-fitting the deep network to the training data. Furthermore, with conventional deep network training techniques, when experimenting with the network architecture during the training process, it is difficult to leverage results of the network trained in previous iterations. Embodiments of the present invention utilize a learning strategy to train a deep neural network architecture that allows building on previous training experiments.

Deep neural networks or deep networks are machine learning based neural networks with multiple hidden layers of learned features or variables between the input data and the output data. Given a pre-trained deep neural network or a deep neural network designed from scratch for a classification problem, confusion/hard samples can be identified based on a softmax response of the deep neural network, and a subsequent specialized network can be trained to handle only the identified confusion samples. The specialized network is built upon the previously trained network's feature space, as opposed to training the specialized network directly from the raw image pixels. In an advantageous embodiment, the output of one of the hidden layers of the initial trained deep network can be used as the input layer to the subsequent specialized network. For example, a pre-selected hidden layer of the initial deep network can be used or multiple hidden layers of the initial deep network can be compared to choose the best performing hidden layer to use as the input to the subsequent specialized network. In an alternative embodiment, this can also be achieved by using any layer of the previous deep network as features combined with any choice of classifier, such as a support vector machine classifier. The initial deep network classifies samples (e.g., endoscopic images) and determines a confidence score for each sample. Based on the confidence scores of the samples, samples that are classified with a high confidence score (i.e., above a threshold) are greedily discarded, and the subsequent specialized network concentrates only on confusion/hard samples (i.e., samples with confidence scores below the threshold). This can be repeated for the samples classified by the specialized network to train additional subsequent specialized networks. Such as series of trained network classifiers including an initial deep network and one or more subsequent specialized networks is referred to herein as a deep decision network (DDN). This has the effect of as the training goes deeper, a series of specialized networks continue to "zoom in" on resolving the challenging cases and keep pruning the examples that are already "solved". The threshold value as each stage of the DDN can be learned using cross-validation.

Figure 3:
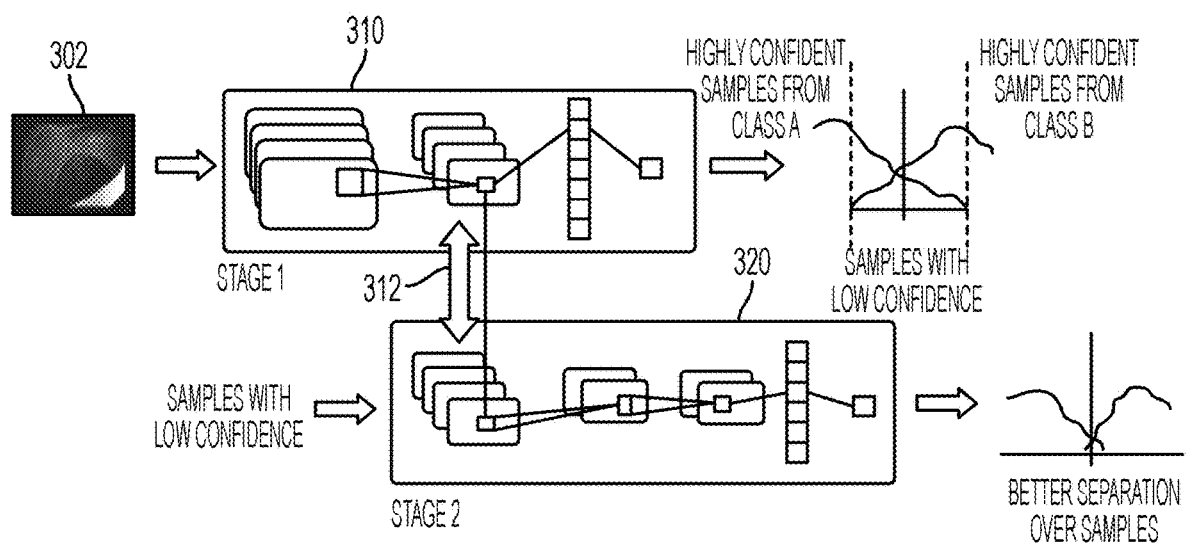
FIG. 3 illustrates an exemplary deep decision network (DDN) according to an embodiment of the present invention.

FIG. 3 illustrates an exemplary deep decision network (DDN) according to an embodiment of the present invention. As shown in FIG. 3, an initial deep network 310 is trained to classify endoscopic images into as class A or class B and to calculate a confidence score for the classification of each endoscopic image. For example, the initial deep network 310 may classify colonoscopic images as positive (containing a polyp) or negative (not containing a polyp), or may classify CLE images a glioblastoma or meningioma. The initial deep network 310 inputs the raw image pixels from an endoscopic image 302 and operates directly on the raw image data to classify the endoscopic image 302. The classification of a large number of samples (endoscopic images) by the initial deep network 310 results in a set of highly confident samples from class A, a set of highly confident samples from class B, and set of samples with low confidence, which are referred to herein as the confused samples. A second deep network 320 is a specialized network that is trained to classify the confused samples that are classified with low confidence by the first deep network 310. The second deep network 320 is built on top of a convolutional layer 312 that is a hidden layer of the first deep network 310. That is, the convolutional layer 312 of the first deep network is used an the input layer of the second deep network 320, and instead of directly inputting the raw image pixels for the low confidence samples, the second deep network 320 uses the output of the convolution layer 312 for a particular sample as a feature vector representing that sample. The classification of the confused samples by the second deep network 320 results in a more accurate separation between the class A samples and the class B samples.

The DDN architecture is trained using a piece-wise training method. The root network (i.e., initial deep network) can be trained using tradition techniques, such as gradient optimization using a back-propagation algorithm. The decision layer of the root network is used to compute its performance and learn a threshold of confidence score for classification using cross-validation. The samples with confidence scores below the learned threshold value are considered to be the hard samples or confusion cases, and these samples are used to train a subsequent specialized network, which can be as simple as a single layer or can be a composition of multiple convolutional layers with fully connected layers. In an exemplary embodiment, the specialized network is trained as a shallow network having a convolutional layer and two fully connected layers, along with some non-linearity and dropout layers. The subsequent network layers are trained only using the confused samples, and the previously trained layers are frozen. Since the specialized network is built on top of a hidden layer in the previous network, the training of the specialized network can be thought of as setting the learning rate of the previously trained network to zero and training newly added layers using only the confused samples. This process can be recursive to train subsequent specialized networks until there are no more confusion/hard samples in the training dataset or until a desired depth of the DDN is met. This allows the newly added layers of the specialized networks to make use of previous layers feature representation and also has a benefit of making early classification decisions for samples with high confidence scores. The piece-wise training of the DDN helps to overcome the problem of over-fitting by training specialized shallow networks that concentrate only on subsets of the entire dataset. In addition, the piece-wise training also helps in avoiding the gradient optimization getting stuck in poor solutions and provides better generalization to unseen data.

Figure 4:
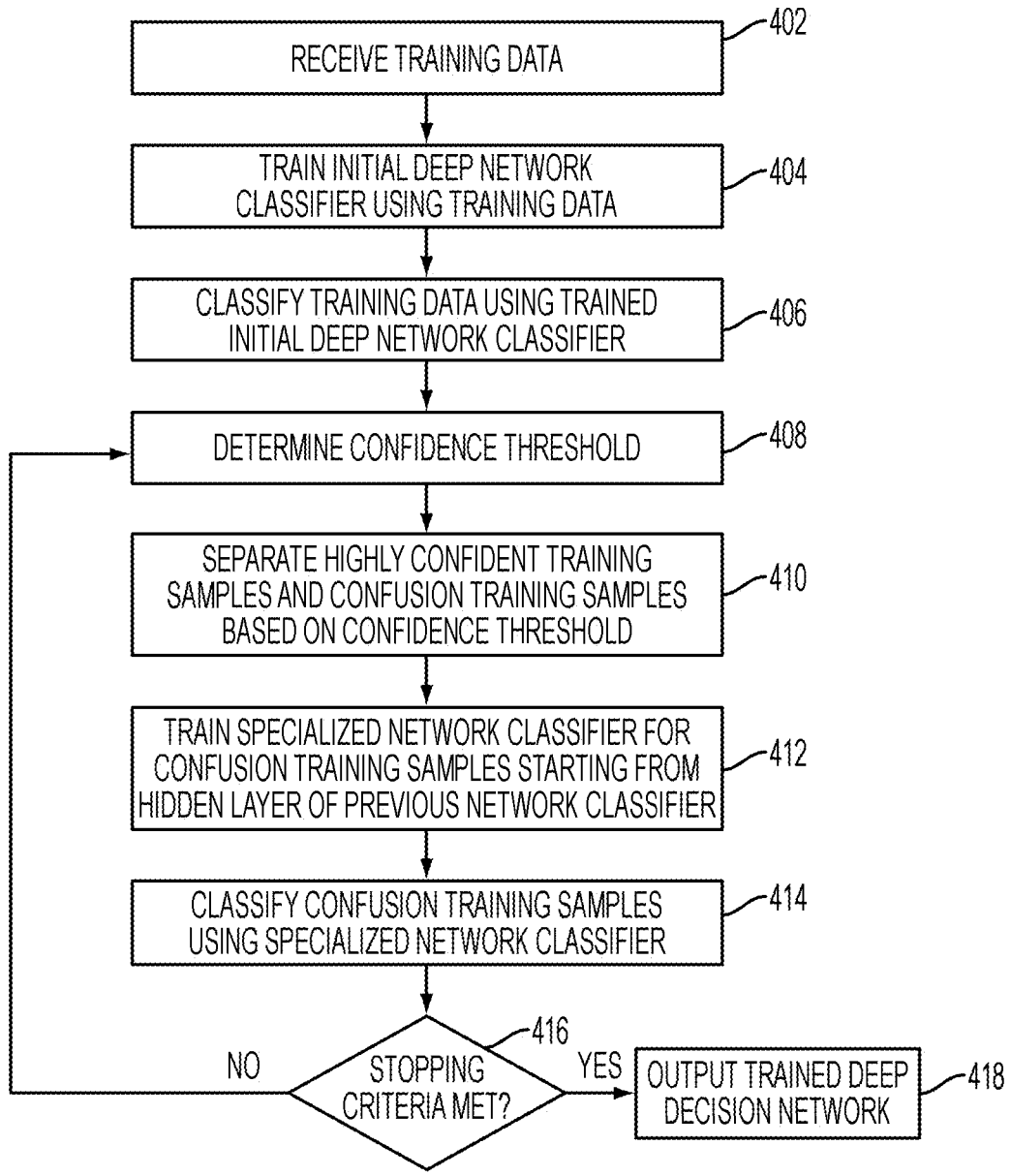
FIG. 4 illustrates a method for training a deep decision network (DDN) for classifying endoscopic images according to an embodiment of the present invention.

FIG. 4 illustrates a method for training a deep decision network (DDN) for classifying endoscopic images according to an embodiment of the present invention. Referring to FIG. 4, at step 402 a set of training data is received. The training data is a set of endoscopic images with known classifications, including a set of positive training samples and a set of negative training samples. The endoscopic images can be acquired using any type of endoscopic or laparoscopic probe. For example, in one embodiment, the training samples may be colonoscopy endoscopic images acquired using a capsulated endoscopic probe. In this the positive training samples can be endoscopic images with polyps present, and the negative training samples can be endoscopic images without polyps present. In another embodiment, the training samples may be CLE images of brain tumor tissue acquired using a CLE probe. In this case, the positive training samples can be CLE images of glioblastoma and the negative training samples can be CLE images of meningioma. The training samples may be preprocessed, for example, to make sure that the training samples have uniform size and resolution. The training samples can be received by loading the training samples from a database or other type of storage or memory. The training samples are randomly divided into a training dataset and a validation dataset.

At step 404, an initial deep network classifier is trained using the training data. In particular, the initial deep network classifier is trained using the training samples in the training dataset. According to an advantageous implementation, the initial deep network classifier is a deep neural network with a plurality of hidden layers that inputs the raw pixel data from the endoscopic images in the training dataset and outputs a classification and a confidence score for each of the endoscopic images in the training dataset. The architecture of the initial deep network classifier can be set based on the classification application, and may include a number of convolutional layers and a number of fully connected layers, along with non-linear functions, pooling, and dropout layers. The initial deep network classifier can be trained using well known deep learning techniques. For example, the initial deep network classifier can be trained using a back-propagation algorithm to perform gradient optimization in order to learn weights and biases for the nodes of each layer that optimizes a cost function that quantifies how well the network's classifications of the endoscopic images in the training dataset matches the expected classifications of those training samples.

At step 406, the training data is classified using the trained initial deep network classifier. The trained initial deep network classifier is applied to each of the endoscopic images in the training dataset and the validation dataset to classify each endoscopic image as positive or negative. The trained deep network classifier also determines a confidence score indicating a confidence level of the classification for each endoscopic image in the training dataset and the validation dataset.

At step 408, a confidence threshold is determined for the current classification stage using the validation dataset. In the first iteration of step 408, the current classification stage refers to the classification of the training data by the trained initial deep network classifier. In each subsequent iteration of step 408, the current classification stage refers to the classification by the most recently trained specialized network classifier. Cross-validation using the classification results and confidence scores for the training samples in the validation dataset resulting from the current classification stage is used to learn the confidence threshold for the current classification stage. The classification results for the training samples in the validation dataset are compared with the ground truth classifications for the training samples in the validation dataset to determine which training samples in the validation dataset have been incorrectly classified. The confidence scores calculated for the incorrectly classified training samples in the validation dataset provide a range of confidence scores at which incorrect classification occurred in the current classification stage. The confidence threshold for the current classification stage can then be determined by selecting a confidence threshold for which all training samples in the validation dataset having a confidence score greater than the confidence threshold were classified correctly in the current classification stage. In an exemplary implementation, the minimum confidence score above which no incorrect classifications occurred for the training samples in the validation dataset can be selected as the confidence threshold.

In an advantageous embodiment of the present invention, individual confidence thresholds may be learned in the current classification stage for different classes. For example, for binary classification, in which each training sample (e.g., endoscopic image) is classified as positive or negative, a first threshold may be learned for positively classified training samples and a second threshold may be learned for negatively classified training samples. The first threshold may be learned by selecting a first confidence value above which no positively classified training samples in the validation dataset were incorrectly classifier, and the second threshold may be learned by selecting a second confidence value above which no negatively classified training samples in the validation dataset were incorrectly classified.

As used herein in the preceding description, a confidence score being "above" or "higher" than another confidence score or the confidence threshold refers to a higher confidence or likelihood that the classification is correct. In a possible implementation, a classification score ranging from 0 to 1 can be calculated for each training sample by the current classifier, where a classification score with a greater numerical value reflects a higher confidence for a positive classification and a lower confidence for a negative classification, and a classification score with a smaller numerical value reflects a higher confidence for a negative classification and a lower confidence for a positive classification. In this case, the confidence score for positively classified samples can be equal to the classification score, and the confidence score for the negatively classified samples can be equal to 1 minus the classification score. Alternatively, the classification score can be used as the confidence score for all training samples, with a lower threshold being defined below which no negatively classified training samples in the validation dataset were incorrectly classified as positive and an upper threshold being defined above which no positively classified training samples in the validation dataset were incorrectly classified as negative.

Figure 5:
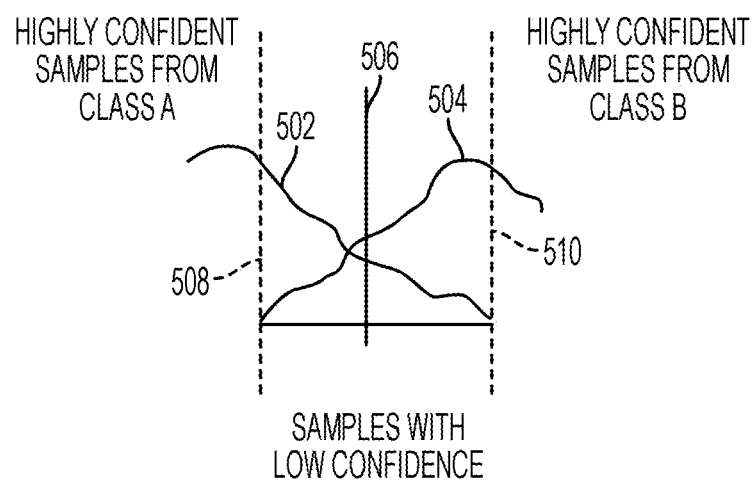
FIG. 5 illustrates learning a confidence threshold according to an embodiment of the present invention.

FIG. 5 illustrates learning a confidence threshold according to an embodiment of the present invention. As shown in FIG. 5, line 502 represents the distribution of samples of class A over a range of classification scores, and line 504 represents the distribution of samples of class B over the range of classification scores. The confidence for class A samples increases as the classification score decreases, and the confidence for class B samples increases as the classification score increases. Line 506 represents the classification score which was used to classify the samples into class A or class B at the current classification stage. All samples having a classification score less than the classification score at line 506 (i.e., all samples to the left of line 506 on lines 502 and 504) were classified in class A. Accordingly, samples on line 504 (class B) to the left of line 506 were incorrectly classified, and threshold 508 represents a confidence threshold for which all samples to the left of threshold 508 are on line 502 and therefore correctly classified in class A. All samples having a classification score greater than the classification score at line 506 (i.e., all samples to the right of line 506 on lines 502 and 504) were classified in class B. Accordingly, samples on line 502 (class A) to the right of line 506 were incorrectly classified, and threshold 510 represents a confidence threshold for which all samples to the right of threshold 510 are on line 504 and therefore correctly classified in class B. In an advantageous implementation, threshold 508 is used as the confidence threshold for samples classified in class A, and threshold 510 is used as the confidence threshold for samples classified as class B. In this case, samples classified with classification scores between the thresholds 508 and 510 are considered low confidence (confused) samples, and samples classified in class A with classification scores less than threshold 508 or classified in class B with classification scores greater than threshold 510 are considered highly confident samples. In an alternative embodiment, the confidence score for samples classified in class A can be equal to 1 minus the classification score, and a single threshold value can be selected by selected the greater of the confidence values corresponding to threshold 508 and threshold 510.

Returning to FIG. 4, at step 410 highly confident training samples and confusion training samples are separated based on the learned confidence threshold. The confidence score for each of the training samples in the training dataset and the validation dataset is compared to the confidence threshold for the current classification stage. If the confidence score for a training sample is higher than the confidence threshold, that training sample is considered to be a highly confident training sample. If the confidence score for a training sample is not higher than the confidence threshold, the training sample is included in the set of confusion training samples. The highly confident training samples from the training dataset and the validation dataset are discarded (i.e., no longer used in the training method). The confusion training samples are preserved and used for training a subsequent specialized network. In an advantageous embodiment, the confusion training samples from the previous training dataset and validation dataset can be combined, and then confusion training samples can be randomly divided into a new training dataset and validation dataset.

At step 412, a specialized network classifier is trained for the confusion samples starting from a hidden layer of the previous network classifier. The specialized network classifier is built from the feature space of the previously trained network classifier and trained only for the confusion training samples from the previous classification stage performed by the previous network classifier. In the first iteration of step 412, a first specialized network classifier is built from the feature space of the trained initial deep network classifier and trained only based on confusion samples resulting from the classification performed by the trained initial deep network. In subsequent iterations, a subsequent specialized network classifier is built from the feature space of the previous specialized network classifier and trained only based on confusion samples resulting from a classification performed by the previous specialized network classifier. In order to train a specialized network classifier built from the feature space of the previous network classifier, a hidden layer in the previous network classifier is used as the input layer of the new specialized network classifier. That is, instead of directly inputting the raw image pixels for the confidence training samples, the new specialized network classifier inputs the output/response of a hidden layer in the previous network classifier for each confusion training sample as a feature vector representing that confusion training sample and is trained classify the confusion training samples based on these feature vectors. In one embodiment, the specialized network classifier can be a deep neural network classifier having multiple hidden layers. In another embodiment, the specialized network classifier can be trained as a shallow network having a convolutional layer and two fully connected layers, along with some non-linearity and dropout layers. The specialized network classifier is trained based on the training dataset of the confusion training samples. The specialized network classifier can be trained using a back-propagation algorithm to perform gradient optimization in order to learn weights and biases for the nodes of each layer that optimizes a cost function that quantifies how well the network's classifications of the confusion training samples starting from the feature vectors output from the hidden layer of the previous network classifier matches the expected classifications of those training samples. The specialized network classifier is trained to classify the confusion training samples and calculate a confidence score for each confusion training sample.

In one embodiment, the specialized network classifier can be built on the feature space of a preset hidden layer from the previous network classifier. In another embodiment, an automated layer selection process can be used to select which hidden layer of the previous network classifier to use as the input layer of the new specialized network classifier. In this case, the validation dataset of the confusion training samples can be used to compare the feature vectors output from different hidden layers from the previous network classifier to determine which hidden layer provides the best basis for classifying the confusion training samples. In an exemplary implementation, a respective specialized network classifier can be trained based on the training dataset of the confusion training samples starting from the feature space of each of the last N (e.g., 2) hidden layers or each of the last N convolutional layers in the previous network classifier. Each of the respective specialized network classifiers is then used to classify the confusion training samples in the validation dataset, and the classification accuracy of the respective specialized network classifiers on the validation dataset is compared to select the most accurate of the respective specialized network classifiers. In an another exemplary implementation, a respective support vector machine (SVM) or other type of machine learning based classifier can be trained on training dataset based on features from each of the last N hidden layers or last N convolutional layers in the previous network classifier. Each SVM (or other type of classifier) is tested on the validation data and the classification accuracy of the SVMs (or other classifiers) is compared to determine which hidden layer of the previous network provides the most discriminative feature space.

At step 414, the confusion training samples from the previous classification stage are classified using the trained specialized network classifier. The trained specialized network classifier is applied to classify each of the confusion training samples in the training dataset and the validation dataset starting with the feature vector output from the hidden layer of the previous network classifier for each confusion training sample. The trained deep network classifier also determines a confidence score indicating a confidence level of the classification for each confusion training sample in the training dataset and the validation dataset.

At step 416, it is determined if a stopping criteria is met. When the stopping criteria is met, the method proceeds to step 418. When the stopping criteria is not met, the method returns to step 408 and repeats steps 408-416. Accordingly, the training method will recursively learn a confidence threshold, separate the remaining training samples into confusion training samples and highly confident training samples, and train subsequent specialized network classifiers until a stopping criteria is met. In an exemplary implementation, these steps can be repeated until there is no confusion training samples remaining or less than a predetermined number of confusion training samples remaining. In this case, when there is no confusion training samples (or less than a predetermined number of confusion training samples) after classification by a specialized network classifier, the stopping criteria is met and the most recently training specialized network classifier is the final specialized network classifier. In another exemplary implementation, the method can recursively generate specialized network classifiers until a preset desired depth of the DDN is met. Another possible stopping criteria is when the most recently trained specialized network classifier fails to discriminate between the remaining confusion training samples. Although in FIG. 4, this step is placed after step 414, it is to be understood that the method can check if the stopping criteria is met at various times while repeating steps 408-414. For example, the method may also check whether the stopping criteria is met after the confusion samples and the highly confident samples are separated and the highly confident samples are discarded in step 410.

At step 418, once the stopping criteria is met, the trained DDN is output. The trained DDN includes the trained initial deep network classifier and one or more specialized network classifiers. The first specialized network classifier is built on the feature space of a hidden layer of the initial deep network classifier, and each subsequent specialized network classifier is built on the feature space of a hidden layer of the previous specialized network classifier. Each specialized network classifier trained only on training samples that were not classified with high confidence by the previous network classifier. The trained DDN can be stored, for example, on a storage or memory of a computer system, and used to classify previously unseen endoscopic images.

Figure 6:
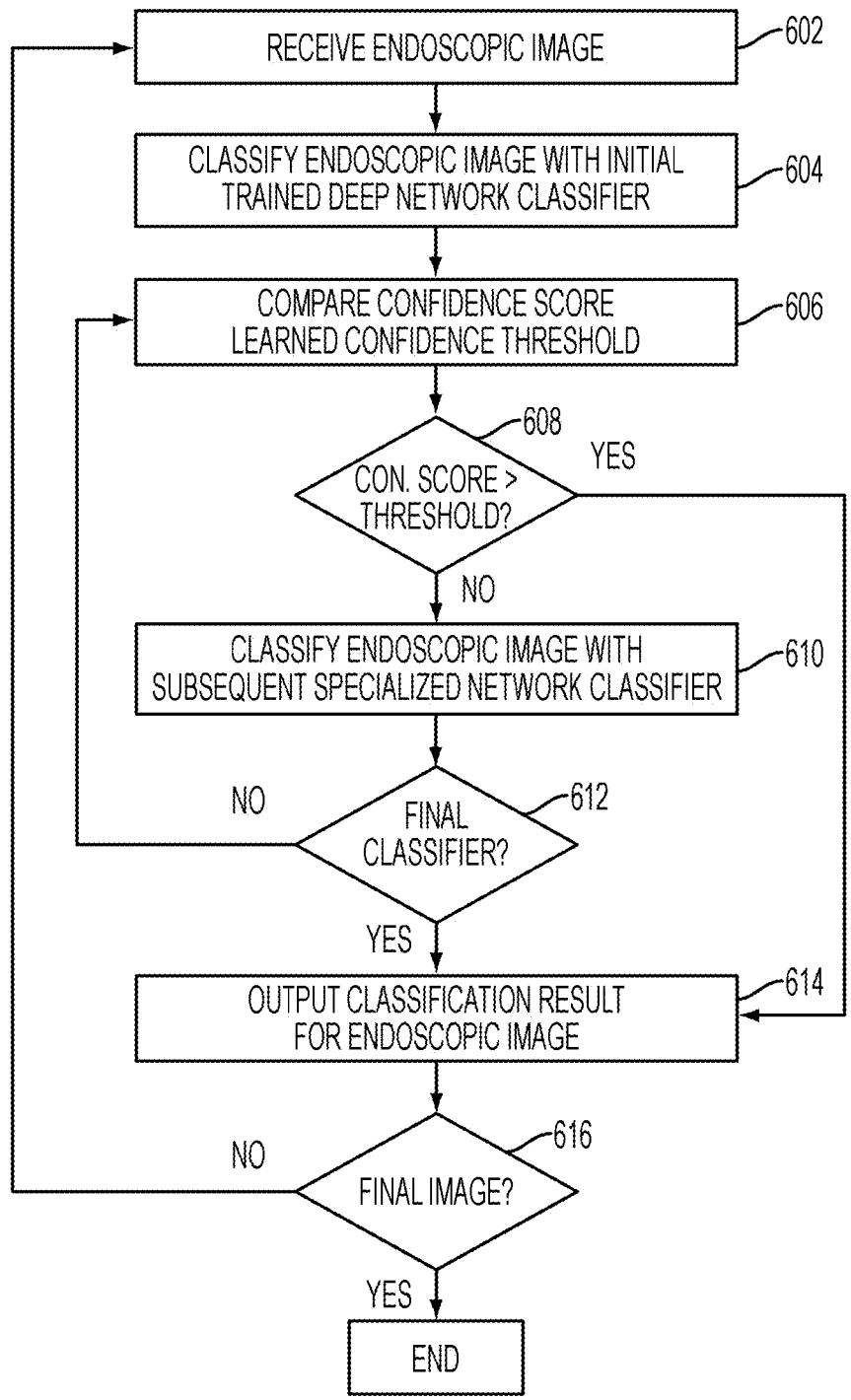
FIG. 6 illustrates a method of classifying endoscopic images using a deep decision network (DDN) according to an embodiment of the present invention.

FIG. 6 illustrates a method of classifying endoscopic images using a deep decision network (DDN) according to an embodiment of the present invention. Referring to FIG. 6, at step 602, an endoscopic image is received. The endoscopic image can be acquired using any type of endoscopic or laparoscopic probe. For example, in one embodiment, the endoscopic image may be a colonoscopic image acquired using a capsulated endoscopic probe. In another embodiment, the endoscopic image may be a CLE image of brain tumor tissue acquired using a CLE probe. The endoscopic image may be received directly from the endoscopic probe or may be received be loading a previously acquired endoscopic image that has been stored on a memory or storage of a computer device. The endoscopic image can be a frame of a video acquired by the endoscopic probe. In this case, the endoscopic image is one of a plurality of endoscopic images in a stream of endoscopic images. In one embodiment, endoscopic images are received from the endoscopic probe in real time as the endoscopic images are acquired and the endoscopic images are classified in real time using the trained deep decision network. In this case, the computer system that is performing the method of FIG. 6 may utilize one or more graphics processing units (GPU).

At step 604, the endoscopic image is classified by an initial trained deep network classifier. According to an advantageous implementation, the initial deep network classifier is a deep neural network with a plurality of hidden layers that inputs the raw pixel data from the endoscopic image and outputs a classification and a confidence score for the endoscopic image. The initial trained deep network classifier can perform a binary classification that classifies the endoscopic image into one of two classes, such as positive or negative. In one embodiment in which the endoscopic image is a colonoscopic image, the initial trained deep network classifier classifies the endoscopic image as positive if a polyp is present in the endoscopic image and classifies the endoscopic image as negative if no polyp is present in the endoscopic image. In another embodiment in which the endoscopic image is a CLE image, the initial trained deep network classifier classifies the endoscopic image as glioblastoma (positive) or meningioma (negative). The confidence score calculated by the initial trained deep network classifier can be an estimated probability of the accuracy of the classification of the endoscopic image by the trained initial deep network classifier. In an advantageous embodiment, the initial trained deep network classifier may be a deep network classifier trained specifically for the particular classification being performed in the method of FIG. 6 using training samples corresponding to the type endoscopic images being classified. In an alternative embodiment, the initial trained deep network classifier may be a pre-trained deep neural network that was not trained using the specific type of endoscopic images that are being classifier. For example, in the initial trained deep network classifier may be a pre-trained convolutional neural network (CNN) whose parameters are learned from a large scale non-medical image database.

At step 606, the confidence score calculated for the endoscopic image is compared with a learned confidence threshold. As described in connection with step 408 of FIG. 4, the learned confidence threshold is learned in the training phase by determining a confidence score threshold above which there are no confusion cases (i.e., no incorrect classifications in a set of training samples). In a possible embodiment, the confidence threshold may be the same for positively and negatively classified endoscopic images. In another possible embodiment, there may be different learned confidence thresholds for positively and negatively classifier endoscopic images. A respective threshold is learned for each classification stage by a respective network classifier. Accordingly, when the endoscopic image is classified by the initial trained deep network classifier, the confidence score calculated for the endoscopic image by the initial trained deep network classifier is compared to a first learned confidence threshold that is trained to evaluate classification by the initial trained deep network classifier. If the method returns to step 606 after classification by a specialized network classifier, the confidence score calculated for the endoscopic image by the specialized network classifier is compared to a different learned threshold that is trained to evaluate classification by that specialized network classifier.

At step 608, it is determined whether the confidence score for the endoscopic image is higher than the confidence threshold. As used herein, a confidence score that is "higher" than the confidence threshold refers to a confidence score that indicates a higher likelihood that the classification of the endoscopic image than the confidence threshold. As discussed above in connection with step 408 of FIG. 4, there may be different ways to implement the confidence score, and in some possible implementation a numerically smaller value may indicate a higher confidence for a certain classification. If it is determine that the confidence score for the endoscopic image is not higher than the confidence threshold, the endoscopic image is considered to be a confusion case and the method proceeds to step 610. If it is determined that the confidence score for the endoscopic image is higher than the confidence threshold, the endoscopic image is considered to be a highly confident case and the method proceeds to step 614, at which the classification result for the endoscopic image is output. Accordingly, endoscopic images that are considered to be confusion cases are further classified by one or more subsequent trained specialized network classifiers, but the classification results for endoscopic images considered to be highly confident cases are output without further classification by a subsequent specialized network classifier.

At step 610, the endoscopic image is classified by a subsequent specialized network classifier. The subsequent specialized network classifier is built on the feature space of the previous network classifier. In particular, if the endoscopic image has only been classified by the initial trained deep network classifier, a first specialized network classifier that is built on the feature space of the initial trained deep network classifier is used to classify the endoscopic image. Instead of inputting the raw pixel data from the endoscopic image, the first specialized network classifier inputs the output of a hidden layer of the initial trained deep network classifier as a feature vector representing the endoscopic image. The first specialized network classifier classifies the endoscopic image and determines a confidence score for its classification of the endoscopic image. The first specialized network classifier is trained based on only confusion cases resulting from classification of training samples by the initial trained deep network classifier.

Each specialized network classifier subsequent to the first specialized network classifier is built on the feature space of the previous specialized network classifier, and inputs the output of a hidden layer of the previous specialized network classifier as a feature vector representing the endoscopic image. Each subsequent specialized network classifier classifies the endoscopic image and determines a confidence score for its classification of the endoscopic image. Each subsequent specialized network classifier is trained based on only confusion cases resulting from classification of training samples by the previous subsequent network classifier.

At step 612, it is determined if the specialized classifier that classified the endoscopic image is step 610 is the final trained specialized classifier in the DDN. If the specialized classifier is not the final trained specialized classifier in the DDN, the method returns to step 606. In this case, the confidence score for the endoscopic image calculated by the specialized network classifier is compared to a learned confidence threshold corresponding to the specialize network classifier (step 606) to determine (at step 608) whether the confidence in the classification of the endoscopic image by the specialized network classifier is high enough to output the classification result or if the endoscopic image is still a confusion case and further classification of the endoscopic image by a subsequent specialized network classifier (step 610) is needed. If the specialized classifier is the final trained specialized classifier in the DDN, the method proceeds to step 614.

At step 614, the classification result for the endoscopic image is output. In a possible implementation, the classification result can be output by displaying an indication of the classification result on a display device. For example, a label indicating the classification result can be displayed on the endoscopic image on the display device, or a color-code indication that uses one color for positive classifications and another color for negative classifications can be displayed on the display device. Such displayed indications can be displayed in real time or near real time as the endoscopic images are acquired. The classification result can also be output by storing the classification result for the endoscopic image on a memory or storage of a computer system. In another possible implementation, an alert, such as a displayed indication or audio alert, can be generated in response to a certain classification (e.g., a positive classification) being output for an endoscopic image. For example, for colon polyp detection or malignant brain tumor detection, a large percentage of the incoming endoscopic images (i.e., frames of an acquired video stream) may be classified as negative. In this case, an alert may be generated to alert the doctor/clinician only when an endoscopic image is classified as positive (e.g., an endoscopic image with a colon polyp or malignant brain tumor tissue is found).

At step 616, it is determined if the endoscopic image is the final endoscopic image in the stream of endoscopic images. If the endoscopic image is the final endoscopic image being classified, the method ends. If the endoscopic image is not the final endoscopic image, the method returns to step 602 and is repeated for the next endoscopic image in the stream of endoscopic images. Accordingly, when applied to a plurality of endoscopic images, the method of FIG. 6 classifies all of the endoscopic images with the initial trained deep classifier, compares a confidence score calculated by the initial trained deep classifier for each endoscopic image with a learned confidence threshold, and determines which endoscopic images are highly confident cases and which endoscopic images are potential confusion cases. The classification results from the initial trained deep network classifier are output for the endoscopic images considered to be highly confident cases, and the endoscopic images considered to be potential confusion cases are further classified with one or more specialized network classifiers.

Deep decision networks with different network architectures can be used for different classification tasks. Exemplary network architectures for polyp/no-polyp classification of colonoscopy endoscopic images and glioblastoma/meningioma classification of CLE images are shown in Table 1. Table 1 provides the types of layers and size of each layer in the DDN architectures for polyp and brain tumor classification. In Table 1, Conv refers to a convolutional layer and FC refers to a fully connected layer. Each Conv layer is followed by a nonlinear activation function rectified linear unit (ReLu) and pooling. Except for the final FC layer, each FC layer is followed by an ReLu and dropout layer with p=0.5. The final FC layer is the decision layer that classifies a sample into one of two classes. In an exemplary implementation for both the polyp classification DDN and brain tumor classification DDN, the first stage (initial deep network classifier) includes all of the layers in Table 1 except the Conv3 (third convolutional) layer. In the second stage, the specialized network classifier is trained by inserting the Conv3 layer after the Conv2 layer, the layers before the insertion are all frozen, the subsequent FC layers are randomly initialized, and the network is retrained using only outputs from Conv2 corresponding to the confusion samples classified in the first stage. Accordingly, a new specialized network is built on top of the feature space of one of the hidden layers (Conv2) of the initial deep network classifier. In an exemplary implementation, a step learning rate policy was adopted for network training in both embodiments (polyp classification and brain tumor classification) with the learning rate set to 0.001, stepwise of 10000, and momentum of 0.9.

TABLE 1

| Dataset | | Convnet Configuration | | | | |
|---|---|---|---|---|---|---|
| Polyp | image (110 × 110 × 3) | Conv1 (64 × 11 × 11) | Conv2 (128 × 5 × 5) | Conv3 (256 × 3 × 3) | FC (512) | FC (2) |
| Brain Tumor | image (110 × 92 × 1) | Conv1 (96 × 11 × 11) | Conv2 (256 × 5 × 5) | Conv3 (384 × 3 × 3) | Two FC's (4096) | FC (2) |

The present inventors tested the above describes methods for classifying endoscopic images using a DDN for brain tumor classification, in which CLE images of brain tumors were classified as glioblastoma or meningioma, and polyp classification, in which colonoscopy endoscopic images were classified as positive (polyp) or negative (no polyp) to flag endoscopic images containing a polyp. In both cases the classification results using the DDN was compared to classification using the following other methods: (1) classification using a bag of visual words (BOW) scale invariant feature transform (SIFT) feature with a support vector machine (SVM) classifier (with a radial basis function (RBF) kernel; (2) ImageNet pre-trained features with an SVM, in which feature vectors extracted from layers of a pre-trained CNN are fed into an SVM; and (3) a traditional deep network (TDN) having the same complexity (number of layers and parameters) and the combined networks of the DDN. For each classification task (brain tumor classification and polyp classification) the TDN used for the classification includes all layers shown in Table 1 trained in a single deep neural network.

In order to perform the classification of brain tumor tissue in CLE images, the CLE images were acquired using a commercially available clinical endo-microscope. The endo-microscope is a probe-based CLE system including a laser scanning unit, software, a flat-panel display, and fiber optic proves providing a circular view with a diameter of 160 μm. The device is intended for imaging the internal microstructure of tissues in the anatomical tract that are accessed by an endoscope. The system is clinically used during an endoscopic procedure for analysis of sub-surface structures of suspicious lesions, which is primarily referred to as optical biopsy. In a surgical resection application, a neurosurgeon inserts a hand-held proof into a surgical bed to examiner the remainder of the tissue to be resected. The equipment was used to collect 117 short videos, each from a unique patient suffering from glioblastoma, and relatively longer videos from patients with meningioma. All videos were captured at 24 frames per second, under a resolution of 464×336. The collection of videos is hereafter referred to as the brain tumor dataset.

Due to the limited imaging capability of CLE devices or intrinsic properties of brain tumor tissues, the resultant images often contain little categorical information and are not useful for recognition algorithms. Image entropy has often been used to quantitatively determine the information content of an image. Specifically, low-entropy images have very little contrast and large runs of pixels with the same or similar values. Pre-processing was performed to filter uninformative video frames from the brain tumor dataset. In particular, an entropy threshold was empirically determined by calculating the distribution of the individual frame entropy throughout the dataset (calculated over 34,443 frames). In this case, the entropy threshold was 4.15. This simple thresholding scheme resulted in 14,051 frames containing glioblastoma and 11,987 frames containing meningioma to be selected. Experimental results of the classification are provided based on a leave pair of patients out (one with glioblastoma and another with meningioma). Further, a center crop was taken of 220×220 square image inscribed in the circular lens region. For all deep learning related experiments (including the DDN classification), the images were resized to 110×92 in order to reduce computational complexity.

Table 2 shows a quantitative performance comparison of the different classification methods on five random splits of images in the brain tumor dataset. As shown in Table 2, the DDN classification method described herein significantly outperforms all of the other methods. In comparison to the TDN, the DDN classification method improves the performance by around 9%, and the DDN method does well in terms of accuracy, sensitivity, and specificity. This provides evidence that the proposed method of building deep networks as DDNs performs better than the traditional way of building deeper networks. In addition, the DDN classification method also provides the benefit that the classification of some images can be stopped early based on the confidence score. This helps in reducing the test time, which becomes significant to achieve real time performance when the network is very deep.

were pre-processed to fix the final image size to be 636×530 (chosen based on the average resolutions of all of the video frames). The lens region was separated from the rest of the black region and then resized (maintaining the aspect ratio) to fi the fixed window size of 636×530. Since the number of frames containing a polyp was relatively low compared to the number of frames with no polyp, only the positive frames were perturbed to generate additional positive training samples. Perturbation involved rotation by angles of 90, 180, and 270 degrees, followed by flipping the image and again rotating with the same set of angles. For all the classification experiments, the resulting images were later resized to 110×110×3.

Figure 7:
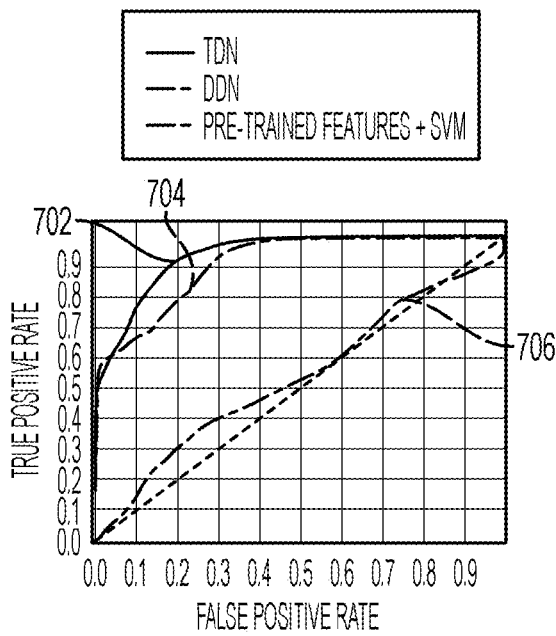
FIG. 7 illustrates receiving operating characteristic (ROC) curves for polyp classification using different classification methods.
Figure 7:
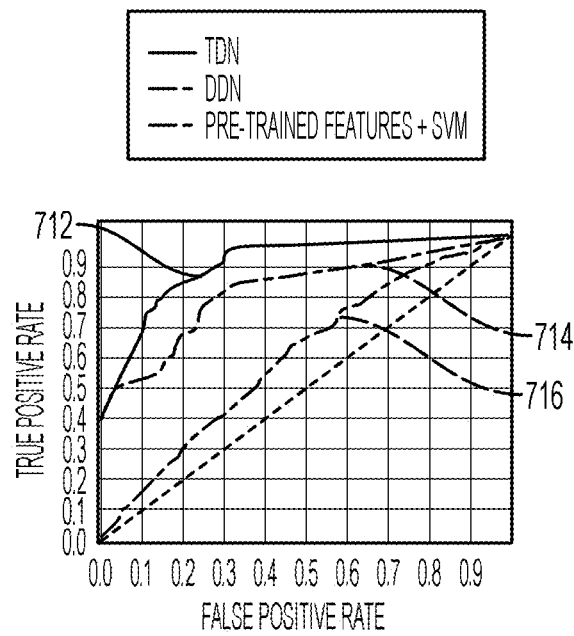
Figure 7:
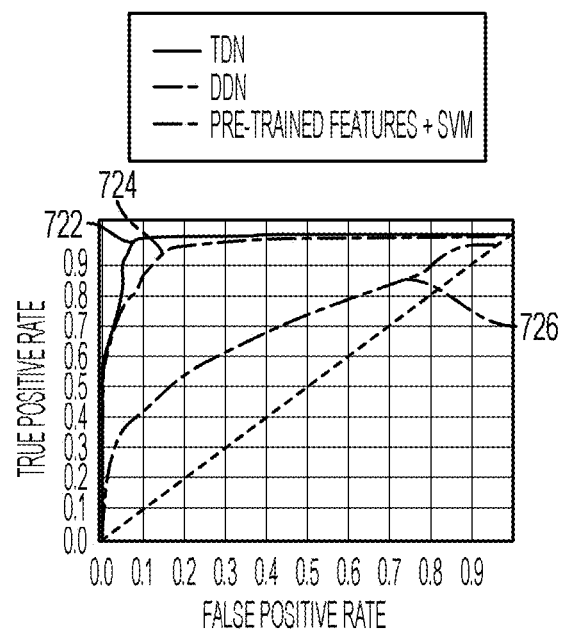
Figure 7:
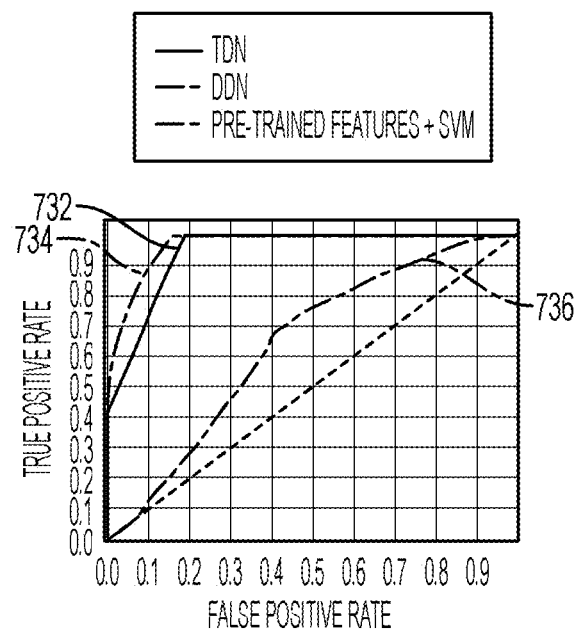

Table 3 shows a quantitative performance comparison of the different classification methods on the four random splits of the polyp classification dataset. As shown in Table 3, similar performances trends as reported for the brain tumor classification can be observed, where the DDN classification method described herein out-performs all other methods. FIG. 7 illustrates receiving operating characteristic (ROC) curves for polyp classification using the different classification methods. As illustrated in FIG. 7, image (a) shows the ROC curves of the DDN classification method 702, the TDN classification 704, the pre-trained features and SVM classification 706 for split 1 of the polyp classification dataset. Image (b) shows the ROC curves of the DDN classification method 712, the TDN classification 714, the pre-trained features and SVM classification 716 for split 2 of the polyp classification dataset. Image (c) shows the ROC curves of the DDN classification method 722, the TDN classification 724, the pre-trained features and SVM classification 726 for split 2 of the polyp classification dataset. Image (d) shows the ROC curves of the DDN classification method 732, the TDN classification 734, the pre-trained features and SVM classification 736 for split 4 of the polyp classification dataset. Overall, the area under the curve is significantly better for the DDN classification method when compared to the other methods, for each of the splits.

TABLE 2

| | SIFT + BOW + SVM(RBF) | | | ImageNet Pre-trained features | | | Traditional Deep Network | | | Deep Decision Network | | |
|---|---|---|---|---|---|---|---|---|---|---|---|---|
| | Acc. | Sen. | Spec. | Acc. | Sen. | Spec. | Acc. | Sen. | Spec. | Acc. | Sen. | Spec. |
| split-1 | 81.44 | 0.9681 | 0.7117 | 66.71 | 0.906 | 0.507 | 77.98 | 0.9138 | 0.6900 | 81.14 | 0.878 | 0.766 |
| split-2 | 63.30 | 0.9747 | 0.4938 | 61.11 | 0.949 | 0.473 | 63.74 | 0.9292 | 0.6900 | 73.24 | 0.979 | 0.631 |
| split-3 | 82.34 | 0.9152 | 0.7504 | 88.65 | 0.971 | 0.862 | 76.94 | 0.7665 | 0.7717 | 88.92 | 0.900 | 0.880 |
| split-4 | 97.94 | 0.9803 | 0.9781 | 95.30 | 0.960 | 0.942 | 93.40 | 0.9338 | 0.9343 | 97.36 | 0.955 | 0.100 |
| split-5 | 76.89 | 0.7008 | 0.8380 | 82.54 | 0.725 | 0.926 | 74.47 | 0.7976 | 0.6911 | 84.9 | 0.703 | 0.997 |
| Overall | 79.28 | | | 78.42 | | | 76.27 | | | 85.82 | | |

The polyp classification experiments were performed on a publically available polyp dataset from ISBI 2014 Challenge on Automatic Polyp Detection in Colonoscopy Videos. The dataset includes 21 short colonoscopy videos from the ASU-Mayo Clinic polyp database, of which 11 videos have a unique polyp inside (positive shots) and the other 10 have no polyps inside (negative shots). Some videos are high resolution but some are recorded in lower resolution. Some videos display a careful colon examination while others show a hasty colon inspection. Some videos have biopsy instruments in them while others do not. The classification experiments were performed on four random splits at the video level.

Since the videos were of different resolutions and the region around the frames were varying, the video frames

TABLE 3

| | SIFT + BOW + SVM(RBF) Acc. | ImageNet Pre-trained features (Conv3) Acc. | TDN Acc. | DDN Acc. |
|---|---|---|---|---|
| split-1 | 89.1 | 88.89 | 78.34 | 87 |
| split-2 | 37.46 | 73.41 | 67.81 | 83 |
| split-3 | 70.82 | 90.95 | 88.88 | 92.75 |
| split-4 | 82.90 | 85.59 | 84.45 | 92.40 |
| Overall | 70.08 | 81.66 | 80.67 | 87.43 |

Figure 8:
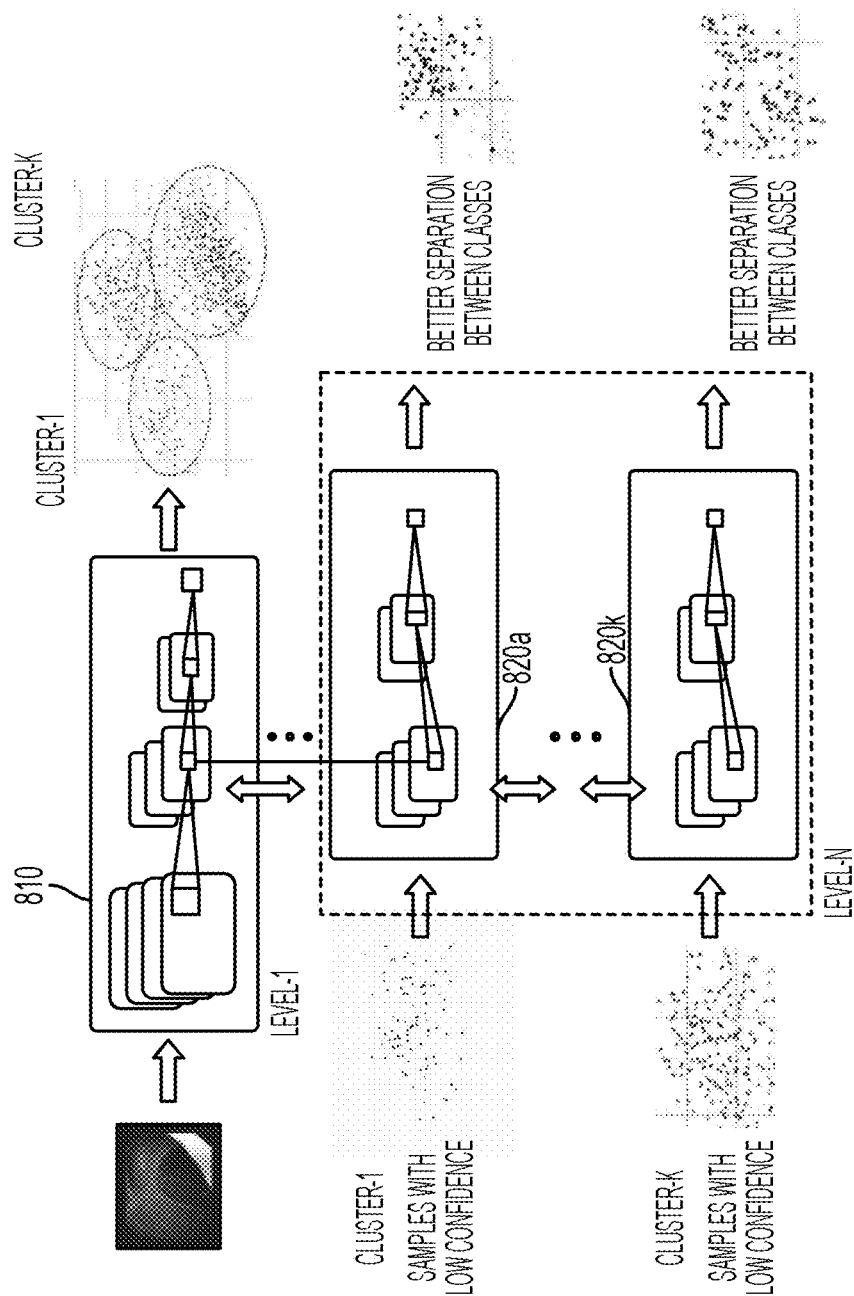
FIG. 8 illustrates an exemplary deep decision network (DDN) for multi-class classification according to an embodiment of the present invention.

In the embodiments described above the deep decision network (DDN) is applied to binary classification tasks in which endoscopic images are classified as positive or negative. In another possible embodiment of the present invention, a DDN can be trained and applied for multi-class classification of medical images in which the images are classified into three or more classes. FIG. 8 illustrates an exemplary deep decision network (DDN) for multi-class classification according to an embodiment of the present invention. As shown in FIG. 8, an initial deep network 810 is trained to classify input images into one of multiple (e.g., three or more) possible classes. Given a training dataset, this initial deep network 810 (i.e., root network) can be trained using the back propagation algorithm. The initial deep network 810 classifies each sample (image) and determines a confidence score for the classification, which is compared to a threshold learned using a validation dataset in training. In training, samples determined to be confusion samples (i.e., having a confidence score less than the learned threshold) are clustered into a plurality of clusters (e.g., K clusters in FIG. 8). In particular, the confusion matrix, computed over the validation dataset, is used to identify clusters of object classes, such that each cluster may have a large confusion among classes inside the cluster but the confusion between the clusters is low. At the subsequent level of the DDN, instead of training a single specialized network classifier, a respective specialized network classifier is trained for data within each of the plurality of clusters to correctly classify the confusion samples (i.e., misclassified samples or low confidence samples) within the respective cluster. As shown in FIG. 8, at level N of the DDN, K specialized network classifiers 820a-820k, each for a corresponding one clusters 1-K. In an advantageous implementation, each of the K specialized network classifiers at a level of the DDN can be a shallow network trained to distinguish between a subset of classes belonging to the respective cluster. This process of building the network can be iterated for multiple levels, for example until no further improvements is achieved on the validations dataset. During testing, an input image is routed through the DDN until its class is determined with a confidence score greater than the learned threshold at a particular network level. If the confidence score for the classification at a particular network level is less than the learned threshold, a cluster is identified for the image (i.e., the image is assigned to clusters of training data learned in training), and the specialized network corresponding to that cluster is used to classify the image at the next level of the DDN.

In an advantageous implementation, the clusters are identified at each level of the multi-class DDN using a spectral co-clustering algorithm. The spectral co-clustering algorithm approximates the normalized cut of a bi-partite graph (symmetric matrix) to find heavy sub-graphs (sub-matrices), thus resulting in block diagonalization of the matrix. The spectral co-clustering algorithm is applied over the co-variance of the confusion matrix, with each block in the resulting block diagonal matrix forming a cluster. Using this clustering algorithm, although different clusters would be disjoint (no overlapping classes), the confusion among the classes within a cluster would be high. Furthermore, if there are any entries (in the confusion matrix) which are not within the diagonal blocks, then the samples contributing to those entries would get miss-classified. Thus, to minimize the likelihood of such miss-classifications, the network parameters are fine-tuned using a joint loss, combining softmax and weighted constrative loss, as explained in greater detail below.

In order to determine the optimal clustering C*, a fitness measure fm(C) is defined, for a given clustering C computed using spectral co-clustering, as:

$$fm(C) = \left(\epsilon + \frac{1}{K}\sum_{i=1}^{K} |C_i|\right)$$

where $\epsilon$ is the miss-classification error introduced due to the data-split, $C_i$ is the $i^{th}$ cluster (set of classes), and $|\cdot|$ is the size of a set. The optimal clustering C* is then given by:

$$C^* = \underset{c}{\arg\min}\, fm(C)$$

As discussed above, errors due to incorrect assignment of samples to clusters are irrecoverable. To minimize such miss-classification errors during data-splitting, the softmax-loss is augmented with an error-driven, weighted contrastive loss function that helps block diagonalization of the confusion matrix. The overall loss function is given by:

$$L = \lambda_1 \times L_m + \lambda_2 \times L_{softmax}$$

where $L_m$ is the weighted contrastive loss function, $L_{softmax}$ is the softmax loss function, and $\lambda_1$ and $\lambda_2$ are weights that control the relative effects of the weighted contrastive loss function $L_m$ and the softmax loss function $L_{softmax}$. In an exemplary embodiment, the weights $\lambda_1$ and $\lambda_2$ were set to 1.0 based on performance on the validation dataset.

The weighted contrastive loss function $L_m$ can be interpreted as a set of soft constraints which impose a significantly higher penalty for miss-classifying a sample to any class belonging to another cluster as compared to the penalty of miss-classifying to a class that belongs to the same cluster. In other words, minimizing the weighted contrastive loss results in a similarity metric of samples belonging to the same cluster to be small and samples across different clusters to be large. The weighted constrative loss function is given by:

$$L_m = w_{ij} \times \left(\frac{1-Y}{2} \times D^2 + \frac{Y}{2} \times \{\max(0, m-D)\}^2\right)$$

where, $$w_{ij} = \begin{cases} 0.1 & \text{if } i \subset C_k \text{ and } j \subset C_k \\ 1 & \text{otherwise} \end{cases}$$

where $w_{ij}$ is the weight corresponding to class labels i and j, D is the $L_2$-norm between a pair of samples, Y is the label representing whether the samples are similar or dissimilar pairs, m is the margin, and $C_k$ represents the $k^{th}$ cluster.

In order to train a multi-class DDN, starting with the initial deep network classifier (root network), its softmax layer is used to compute the performance and learn a classification threshold for each class using cross-validation. This threshold is used during testing to make an early decision on samples. The confusion matrix is then computed on the validation dataset and used to identify the clusters of confusion cases. Next, the network is fine-tuned using the weighted contrastive loss function. The weights for the weighted contrastive loss function are determined based on the confusion matrix. After fine-tuning, the samples are split according to their cluster IDs. For each cluster, a respective specialized network classifier is added to the decision network. Each specialized network classifier can be a shallow network trained to distinguish between a subset of classes belonging to that cluster. Each specialized network is built on the feature space of the previous level classifier in the DDN. That is, when the new layers are trained for a particular specialized network classifier, the previously trained layers are frozen by setting their learning rate to zero. The process of adding specialized network classifiers to the DDN can be continued recursively until there is no more improvement on the validation dataset and/or until a maximum depth of the DDN is reached.

Figure 9:
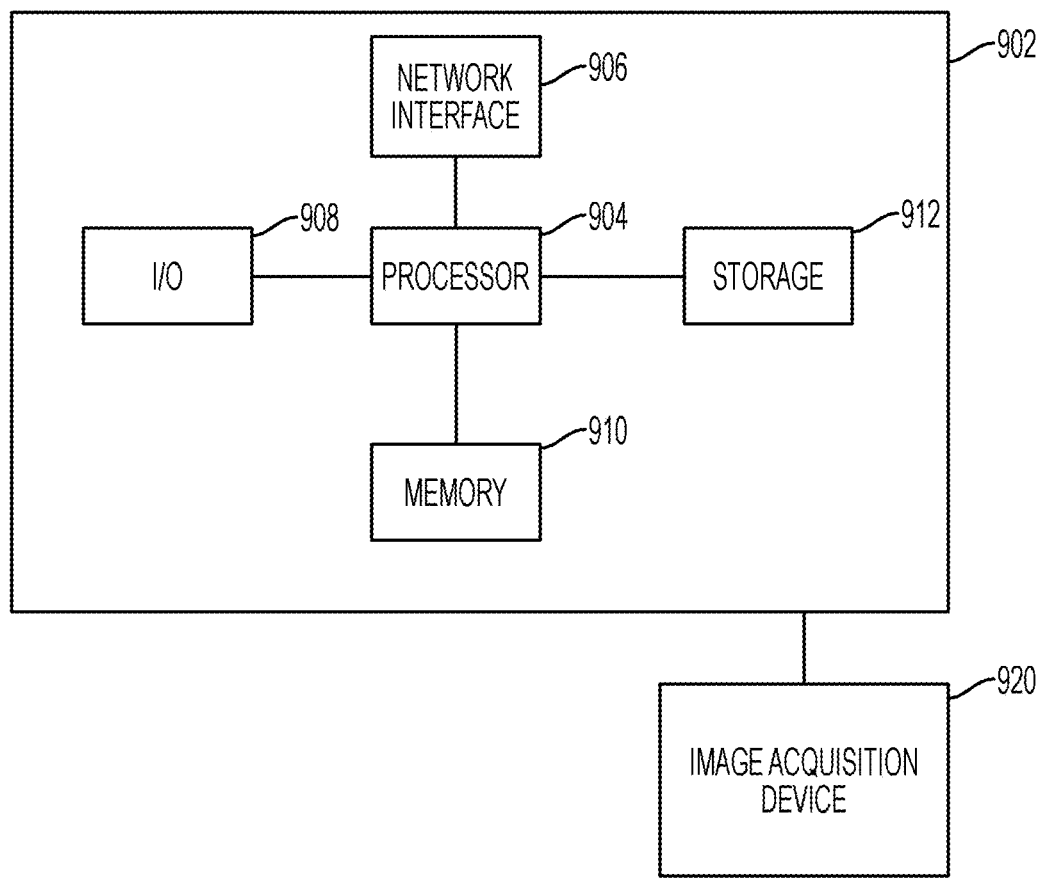
FIG. 9 is a high-level block diagram of a computer capable of implementing the present invention.

The above-described methods for training a deep decision network (DDN) and classifying endoscopic images can be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 4 and 6 may be defined by the computer program instructions stored in the memory 910 and/or storage 912 and controlled by the processor 904 executing the computer program instructions. An image acquisition device 920, such as endoscope or CLE system, can be connected to the computer 902 to input image data to the computer 902. It is possible to implement the image acquisition device 920 and the computer 902 as one device. It is also possible that the image acquisition device 920 and the computer 902 communicate wirelessly through a network. In a possible embodiment, the computer 902 may be located remotely from the image acquisition device 920, and the computer 902 may perform method steps as part of a server or cloud based service. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for classifying endoscopic images, comprising:
   classifying an endoscopic image and determining a confidence score for the endoscopic image using an initial trained deep network classifier;
   comparing the confidence score for the endoscopic image to a learned confidence threshold;
   in response to a determination that the confidence score for the endoscopic image is higher than the learned confidence threshold, outputting the classification of the endoscopic image by the initial trained deep network classifier; and
   in response to a determination that the confidence score for the endoscopic image is not higher than the learned confidence threshold, classifying the endoscopic image with a first specialized network classifier built on a feature space of the initial trained deep network classifier,
   wherein the learned confidence threshold is a confidence score for which no training samples in a validation dataset of training data were incorrectly classified by the initial trained deep network classifier.

2. The method of claim 1, wherein comparing the confidence score for the endoscopic image to a learned confidence threshold comprises:
   comparing the confidence score for the endoscopic image to a first leaned confidence threshold if the endoscopic image is classified into a first class by the initial trained deep network classifier; and
   comparing the confidence score for the endoscopic image to a second learned confidence threshold if the endoscopic image is classified into a second class by the initial trained deep network classifier.

3. The method of claim 1, wherein an input layer of the initial trained deep network classifier inputs raw pixel data of the endoscopic image, and an input layer of the first specialized network classifier inputs a feature vector output by a hidden layer of the initial trained deep network classifier.

4. The method of claim 1, wherein the first specialized network classifier is trained based on only training samples classified by the initial trained deep network classifier having confidence scores lower than the learned confidence threshold.

5. The method of claim 1, further comprising, in response to classifying the endoscopic image with the first specialized network classifier:
   comparing a second confidence value determined for the endoscopic image by the first specialized network classifier to a second learned confidence threshold;
   in response to a determination that the second confidence score for the endoscopic image is higher than the second learned confidence threshold, outputting the classification of the endoscopic image by the first specialized network classifier; and
   in response to a determination that the second confidence score for the endoscopic image is not higher than the second learned confidence threshold, classifying the endoscopic image with a second specialized network classifier built on a feature space of the first specialized network classifier.

6. The method of claim 5, wherein the second learned confidence threshold is a confidence score for which no training samples in a validation dataset of training data were incorrectly classified by the first specialized network classifier.

7. The method of claim 5, wherein an input layer of the second specialized network classifier inputs a feature vector output by a hidden layer of the first specialized network classifier.

8. The method of claim 7, wherein the second specialized network classifier is trained based on only training samples classified by the first specialized network classifier having second confidence scores lower than the second learned confidence threshold.

9. The method of claim 1, wherein the endoscopic image is a frame of a colonoscopy video, and classifying the endoscopic image comprises:
   classifying the endoscopic image as positive or negative, wherein a positive classification indicates that a polyp is present in the endoscopic image and a negative classification indicates the no polyp is present in the endoscopic image.

10. The method of claim 1, wherein the endoscopic image is a confocal laser endomicroscopy image of brain tumor tissue, and classifying the endoscopic image comprises:
   classifying the endoscopic image as glioblastoma tissue or meningioma tissue.

11. The method of claim 1, wherein classifying an endoscopic image and determining a confidence score for the endoscopic image using an initial trained deep network classifier comprises classifying the endoscopic image as one of a plurality of classes comprising three or more classes, and classifying the endoscopic image with a first specialized network classifier built on a feature space of the initial trained deep network classifier comprises:
   identifying a cluster for the endoscopic image from a plurality of learned clusters, each cluster corresponding to a respective subset of the plurality of classes;
   selecting the first specialized network classifier based on the identified cluster from a plurality of specialized network classifiers, each trained for a respective one of the plurality of learned clusters; and
   classifying the endoscopic image as one of the subset of classes corresponding to the identified cluster with the first specialized network classifier.

12. The method of claim 11, wherein the initial trained deep network classifier is fine-tuned using a weighted contrastive loss function to penalize miss-classifications of training images into classes not within the same cluster as ground truth classes for the training images with a greater penalty as compared with miss-classifications of training images into classes within the same cluster as ground truth classes for the training images.

13. A method of classifying endoscopic images, comprising:
   receiving a plurality of endoscopic images;
   classifying each of the plurality of endoscopic images and determining a confidence score for each of the plurality of endoscopic images using an initial trained deep network classifier;
   comparing the confidence score for each of the plurality of endoscopic images to a learned confidence threshold to determine a highly confident subset of the plurality of endoscopic images and a confusion subset of the plurality of endoscopic images;
   outputting classification results from the initial trained deep network classifier for the highly confident subset of the plurality of endoscopic images; and
   classifying each of the confusion subset of the plurality of endoscopic images using one or more specialized network classifiers,
   wherein classifying each of the confusion subset of the plurality of endoscopic images using one or more specialized network classifiers comprises:
      classifying of the endoscopic images in the confusion subset using a first specialized network classifier built on a feature space of the initial trained deep network classifier.

14. The method of claim 13, wherein classifying each of the confusion subset of the plurality of endoscopic images using one or more specialized network classifiers further comprises:
   comparing a second confidence score for each of the endoscopic images in the confusion subset determined by the first specialized network classifier to a second learned confidence threshold to determine highly confident cases and confusion cases of the endoscopic images classified by the first specialized network classifier;
   outputting classification results from the first specialized network classifier for the highly confident cases of the endoscopic images classified by the first specialized network classifier; and
   classifying the confusion cases of the endoscopic images classified by the first specialized network classifier by one or more subsequent specialized network classifiers, wherein each subsequent specialized network classifier is built on a feature space of the previous specialized network classifier and each subsequent specialized network classifier classifies only confusion cases of endoscopic images classified by the previous specialized network classifier.

15. An apparatus for classifying endoscopic images, comprising:
   means for classifying endoscopic images and determining confidence scores for the endoscopic images using an initial trained deep network classifier;
   means for comparing the confidence score for each endoscopic image classified by the initial trained deep network classifier to a learned confidence threshold; and
   means for classifying endoscopic images with confidence scores lower than the learned confidence threshold with a first specialized network classifier built on a feature space of the initial trained deep network classifier
   wherein an input layer of the initial trained deep network classifier inputs raw pixel data of endoscopic images, and an input layer of the first specialized network classifier inputs a feature vector output by a hidden layer of the initial trained deep network classifier.

16. The apparatus of claim 10, wherein the means for comparing the confidence score for each endoscopic image classified by the initial trained deep network classifier to a learned confidence threshold comprises:
   comparing the confidence score for each endoscopic image classified into a first class by the initial trained deep network classifier to a first leaned confidence threshold; and
   comparing the confidence score for each endoscopic image classified into a second class by the initial trained deep network classifier to a second leaned confidence threshold.

17. The apparatus of claim 10, wherein the learned confidence threshold is a confidence score for which no training samples in a validation dataset of training data were incorrectly classified by the initial trained deep network classifier.

18. The apparatus of claim 10, wherein the first specialized network classifier is trained based on only training samples classified by the initial trained deep network classifier having confidence scores lower than the learned confidence threshold.

19. The apparatus of claim 10, further comprising:
   means for comparing, for each of the endoscopic images classified by the first specialized network classifier, a second confidence value determined by the first specialized network classifier to a second learned confidence threshold; and means for classifying endoscopic images with second confidence values lower than the second learned confidence threshold using a second specialized network classifier built on a feature space of the first specialized network classifier.

20. The apparatus of claim 19, wherein the second learned confidence threshold is a confidence score for which no training samples in a validation dataset of training data were incorrectly classified by the first specialized network classifier.

21. The apparatus of claim 20, wherein the second specialized network classifier is trained based on only training samples classified by the first specialized network classifier having second confidence scores lower than the second learned confidence threshold.

22. The apparatus of claim 19, wherein an input layer of the second specialized network classifier inputs a feature vector output by a hidden layer of the first specialized network classifier.

23. A non-transitory computer readable medium storing computer program instructions for classifying endoscopic images, the computer program instructions when executed by a processor perform operations comprising:
classifying an endoscopic image and determining a confidence score for the endoscopic image using an initial trained deep network classifier;
comparing the confidence score for the endoscopic image to a learned confidence threshold;
in response to a determination that the confidence score for the endoscopic image is higher than the learned confidence threshold, outputting the classification of the endoscopic image by the initial trained deep network classifier; and
in response to a determination that the confidence score for the endoscopic image is not higher than the learned confidence threshold, classifying the endoscopic image with a first specialized network classifier built on a feature space of the initial trained deep network classifier
wherein an input layer of the second specialized network classifier inputs a feature vector output by a hidden layer of the first specialized network classifier.

24. The non-transitory computer readable medium of claim 23, wherein comparing the confidence score for the endoscopic image to a learned confidence threshold comprises:
comparing the confidence score for the endoscopic image to a first leaned confidence threshold if the endoscopic image is classified into a first class by the initial trained deep network classifier; and
comparing the confidence score for the endoscopic image to a second learned confidence threshold if the endoscopic image is classified into a second class by the initial trained deep network classifier.

25. The non-transitory computer readable medium of claim 23, wherein the learned confidence threshold is a confidence score for which no training samples in a validation dataset of training data were incorrectly classified by the initial trained deep network classifier.

26. The non-transitory computer readable medium of claim 23, wherein an input layer of the initial trained deep network classifier inputs raw pixel data of the endoscopic image, and an input layer of the first specialized network classifier inputs a feature vector output by a hidden layer of the initial trained deep network classifier.

27. The non-transitory computer readable medium of claim 23, wherein the first specialized network classifier is trained based on only training samples classified by the initial trained deep network classifier having confidence scores lower than the learned confidence threshold.

28. The non-transitory computer readable medium of claim 23, further comprising, in response to classifying the endoscopic image with the first specialized network classifier:
comparing a second confidence value determined for the endoscopic image by the first specialized network classifier to a second learned confidence threshold;
in response to a determination that the second confidence score for the endoscopic image is higher than the second learned confidence threshold, outputting the classification of the endoscopic image by the first specialized network classifier; and
in response to a determination that the second confidence score for the endoscopic image is not higher than the second learned confidence threshold, classifying the endoscopic image with a second specialized network classifier built on a feature space of the first specialized network classifier.

29. The non-transitory computer readable medium of claim 28, wherein the second learned confidence threshold is a confidence score for which no training samples in a validation dataset of training data were incorrectly classified by the first specialized network classifier.

30. The non-transitory computer readable medium of claim 28, wherein the second specialized network classifier is trained based on only training samples classified by the first specialized network classifier having second confidence scores lower than the second learned confidence threshold.

31. The non-transitory computer readable medium of claim 23, wherein the endoscopic image is a frame of a colonoscopy video, and classifying the endoscopic image comprises:
classifying the endoscopic image as positive or negative, wherein a positive classification indicates that a polyp is present in the endoscopic image and a negative classification indicates the no polyp is present in the endoscopic image.

32. The non-transitory computer readable medium of claim 23, wherein the endoscopic image is a confocal laser endomicroscopy image of brain tumor tissue, and classifying the endoscopic image comprises:
classifying the endoscopic image as glioblastoma tissue or meningioma tissue.

* * * * *